(12) United States Patent
Barton

(10) Patent No.: US 11,364,357 B1
(45) Date of Patent: Jun. 21, 2022

(54) PHARYNGEAL RESPIRATORS

(71) Applicant: Casey D. Barton, Chapel Hill, NC (US)

(72) Inventor: Casey D. Barton, Chapel Hill, NC (US)

( * ) Notice: Subject to any disclaimer, the term of this patent is extended or adjusted under 35 U.S.C. 154(b) by 0 days.

(21) Appl. No.: 17/471,931

(22) Filed: Sep. 10, 2021

(51) Int. Cl.
*A61M 16/04* (2006.01)
*A61M 16/06* (2006.01)
*A61M 16/08* (2006.01)
*A61M 16/10* (2006.01)

(52) U.S. Cl.
CPC .... *A61M 16/0488* (2013.01); *A61M 16/0666* (2013.01); *A61M 16/0875* (2013.01); *A61M 2016/103* (2013.01)

(58) Field of Classification Search
CPC .... A61M 16/04–0431; A61M 16/0461; A61M 16/0486–0495; A61M 16/0666–0677; A61M 16/08; A61M 16/0816; A61M 16/0833–0858; A61M 16/0875; A61M 2016/103; A61B 7/023
See application file for complete search history.

(56) References Cited

U.S. PATENT DOCUMENTS

| | | | |
|---|---|---|---|
| 5,513,627 A | 5/1996 | Flam | |
| 6,142,144 A | 11/2000 | Pacey | |
| 6,626,169 B2 | 9/2003 | Gaitini | |
| 7,278,420 B2 | 10/2007 | Ganesh et al. | |
| 9,265,904 B2* | 2/2016 | Esnouf | A61M 16/0463 |
| 9,398,837 B2 | 7/2016 | Vazales et al. | |
| 10,806,901 B2 | 10/2020 | Burkholz et al. | |
| 2012/0180791 A1* | 7/2012 | Ciccone | A61M 16/0486 128/204.18 |
| 2013/0247907 A1* | 9/2013 | Brain | A61M 16/0443 128/202.16 |
| 2021/0290879 A1* | 9/2021 | Swartz | A61M 16/0434 |

* cited by examiner

*Primary Examiner* — Elliot S Ruddie
(74) *Attorney, Agent, or Firm* — Miller IP Law LLC

(57) ABSTRACT

Described herein are examples of pharyngeal respirators. Pharyngeal respirators may include a connection end having a first outer width, a flange disposed on the connection end having a second outer width greater than the first outer width, and a socket disposed on the flange. The connection end may be insertably disposed within a receiver of a pharyngeal breathing tube. The flange may not fit within the receiving end of the pharyngeal breathing tube. The socket may receive a medical fitting. The connection end, the flange, and the socket may form a tubular structure having a first end comprising the connection end and a second end comprising the socket.

18 Claims, 6 Drawing Sheets

PHARYNGEAL RESPIRATORS

BACKGROUND

Whether for induced reasons (e.g., surgery) or situational reasons (e.g., the patient cannot breathe on their own), a healthcare patient may need assistance in maintaining oxygen delivery to their lungs. Airway and respiratory devices are used frequently in various medical fields where a healthcare provider must provide for oxygen delivery to patient's respiratory system. It is further often medically desirable to measure a carbon dioxide content or level of a patient's aspirated air on exhale.

BRIEF DESCRIPTION OF THE DRAWINGS

The present description will be understood more fully when viewed in conjunction with the accompanying drawings of various examples of pharyngeal respirators. The description is not meant to limit the pharyngeal respirators to the specific examples. Rather, the specific examples depicted and described are provided for explanation and understanding of pharyngeal respirators. Throughout the description the drawings may be referred to as drawings, figures, and/or FIGs.

DETAILED DESCRIPTION

Figure 1A:
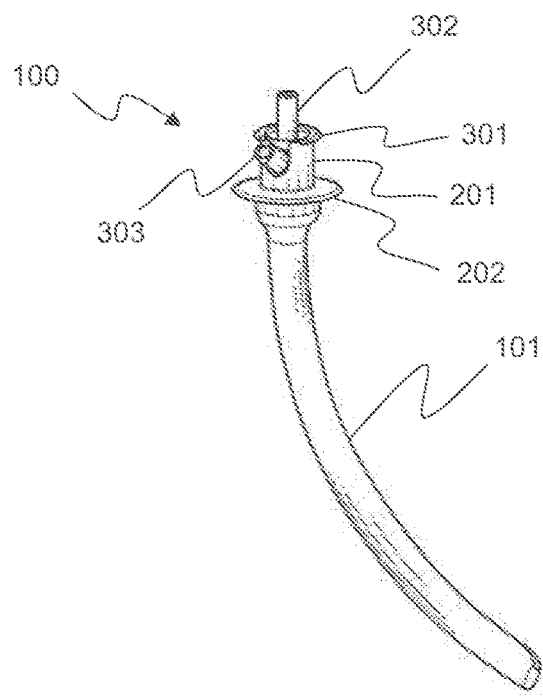
FIG. 1A illustrates a nasal trumpet connected to a fitting using an adapter, according to an embodiment.

Pharyngeal respirators as disclosed herein will become better understood through a review of the following detailed description in conjunction with the figures. The detailed description and figures provide merely examples of the various embodiments of pharyngeal respirators. Many variations are contemplated for different applications and design considerations; however, for the sake of brevity and clarity, all the contemplated variations may not be individually described in the following detailed description. Those skilled in the art will understand how the disclosed examples may be varied, modified, and altered and not depart in substance from the scope of the examples described herein.

Conventional respiration devices may include implements for delivering oxygen to a patient's airway. For example, a conventional respiration device may include a cannula or nasal trumpet, which may be inserted via a patient's nose or mouth, that may assist in delivery of oxygen near a desired location in a patient's airway. For example, in a scenario using a nasal trumpet, the nasal trumpet may have a plastic fitting which may be connected to a medical circuit, for example a tube connected to a supply of oxygen or other breathing gas mixture, or an anesthetic gas. Alternately, a mask may be used to cover a patient's mouth and nose and deliver oxygen to the patient's airway. Conventionally, measurement of carbon dioxide levels in a patient's aspirated air may be performed at a connection (e.g., a tap or a port), proximate a portion of the implement exposed from the patient's mouth or nose, or via a tubing inserted into a cannula used for oxygen delivery.

Such conventional solutions may present difficulties in accurately measuring carbon dioxide levels in a desired part of a patient's airway. If carbon dioxide is to be measured using a connection proximate the portion of the decide exposed outside of the patient's airway, the reading may not accurately reflect carbon dioxide levels proximate a patient's trachea. If carbon dioxide is to be measured using tubing inserted through a cannula, the tubing may affect delivery of oxygen and/or aspiration via the cannula. Furthermore, the tubing may bind in the cannula, block all or a portion of the cannula, or otherwise not be inserted to the proper length through the cannula.

Implementations of pharyngeal respirators may address some or all of the problems described above. Pharyngeal respirators may include apparatuses for modular oropharyngeal and nasopharyngeal airways, which may include an adapter to provide for the connection of various medical components or fittings to a trumpet or airway. Pharyngeal respirators may include a connection end having a first outer width, a flange disposed on the connection end having a second outer width greater than the first outer width, and a socket disposed on the flange. The connection end may be insertably disposed within a receiver of a pharyngeal breathing tube. The flange may not fit within the receiving end of the pharyngeal breathing tube. The socket may receive a medical fitting. The connection end, the flange, and the socket may form a tubular structure having a first end including the connection end and a second end including the socket.

A pharyngeal breathing tube may be used to deliver a medical gas (e.g., oxygen, breathing air, anesthetic gas, or other medical gases). Examples of pharyngeal breathing tubes may include nasal trumpets (e.g., for insertion through a patient's nose) or oral airways (e.g., for insertion through a patient's mouth). Pharyngeal breathing tubes herein may include a divider, which may separate channels within the pharyngeal breathing tube. For example, a pharyngeal breathing tube may have a divider, which may define a first channel and a second channel within the pharyngeal breathing tube. The existence of a first channel and a second channel may provide for the pharyngeal breathing tube to allow for both delivery of a medical gas to an inserted end as well as measurement of a gas level or concentration at the inserted end without interfering with the flow of the medical gas to the inserted end.

A pharyngeal breathing tube may have an insertion end, a body, and a receiving end. The receiving end may include a receiver for receiving an adapter. The receiving end may have a receiving end surface, which may be external to a patient when the pharyngeal breathing tube may be at least partially inserted into the patient's nose or mouth. The insertion end may be inserted into the patient's airway via the patient's nose or mouth such that the receiving end remains external to the patient's airway. The body of the pharyngeal breathing tube may be curved such that it fits into the patient's airway.

The pharyngeal respirator may include a fitting, which may receive, for example, an oxygen tube via a nozzle. The fitting for connection to the oxygen tube may provide for delivery of oxygen to a location proximate a patient's glottic opening. In some embodiments, the fitting may be removed from an intermediate universal fitting on the adapter, which may be used to connect to other medical instruments or tubing. The same adapter may be included in various embodiments, including, inter alia, embodiments implemented for adult airway sizes 110 mm, 100 mm, 90 mm, and 80 mm, as well as child airway sizes 70 mm, 60 mm, and 50 mm and may be integrated with existing stock breathing apparatuses.

By inserting the apparatus into a patient's airway such that an end may be proximate the patient's glottic opening and the soft tissue of the patient's epiglottis may be displaced, the apparatus may facilitate assisted breathing or oxygen delivery for the patient. Further, a channel of the apparatus present for measuring carbon dioxide levels proximate the patient's glottic opening while in use.

Pharyngeal respirators provide for an integrated apparatus. They may prevent misplacement or misdirection of air including oxygen. They may provide for measurement of carbon dioxide of aspirated air on exhale proximate the glottic opening.

FIG. 1A illustrates a system 100 including a nasal trumpet 101 connected to a fitting 301 using an adapter 201, according to an embodiment. The system 100 may provide for, via the patient's nose, the delivery and/or extraction of oxygen or other medical gases (e.g., anesthetic gases) from a patient's airway, as well as measurement of levels or concentrations of another gas or gases, for example, carbon dioxide, in the patient's airway.

The system 100 may include the nasal trumpet 101, the adapter 201, and the fitting 301. The nasal trumpet 101 may have a profile and geometry to fit into a patient's nasal cavity and/or airway. The profile of the nasal trumpet 101 may be, for example, curved, to fit and be insertable into a patient's nasal cavity and airway via the patient's nose. The fitting 301 may have a nozzle 302 and a port 303. In an example, the nozzle 302 may extend from the fitting 301 such that its axis may be collinear with an axis of the fitting 301 and the port 303 may extend from the fitting 301 such that its axis may be at an angle to the axis of the fitting 301. In an example, the nozzle 302 and the port 303 may extend from the fitting 301 such that their axes are at angles to the axis of the fitting 301. In another example, the nozzle 302 and the port 303 may extend such that their axes are parallel to an axis of the fitting 301.

The nozzle 302 may be sized to receive a medical tubing, for example, for the delivery of oxygen or other medical gases into the system 100. The adapter 201 may have a flange 202 to prevent over insertion or slippage, and the adapter 201 may fit into an end of the nasal trumpet 101. To effect this, the nasal trumpet 101 may have a female receiver at an end which may receive a male connector of the adapter 201. The adapter 201 may have a socket which may receive a male connector of the fitting 301.

Figure 1B:
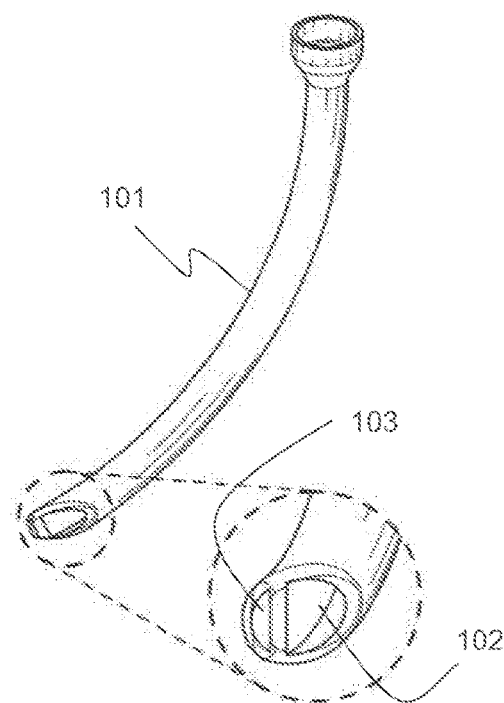
FIG. 1B illustrates a nasal trumpet, according to an embodiment.

FIG. 1B illustrates a nasal trumpet, according to an embodiment. The nasal trumpet 101 may have dual channels. A first channel 102 may provide for the delivery and/or extraction of gases to or from a desired point (e.g., an insertion depth) within a patient's airway. Such delivery or extraction may be via a nozzle (e.g., the nozzle 302 of the fitting 301) in fluid communication with the first channel 102. A second channel 103 may provide for measuring a concentration of a gas (e.g., carbon dioxide) at the desired point in the patient's airway. The second channel 103 may be in fluid communication with, for example the port 303 of the fitting 301. Measurement of a concentration of gas (e.g., carbon dioxide) in the patient's airway may provide insight as to how well the patient may be breathing, how well the patient's lungs are functioning, or other medically relevant insights. A state of being in fluid communication may refer to portions of a system or apparatus forming an open or closed cavity through which a fluid (e.g., a liquid, a gas, or a mixture thereof) may flow as constrained by the open or closed cavity.

Figure 1C:
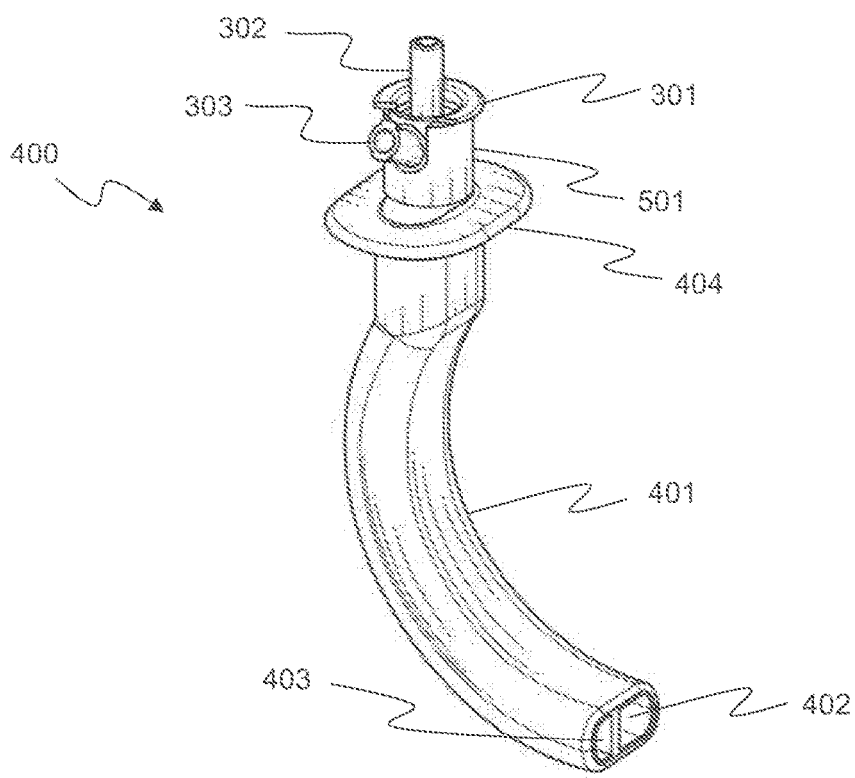
FIG. 1C illustrates an oral airway connected to a fitting using an adapter, according to an embodiment.

FIG. 1C illustrates a system 400 including an oral airway 401 connected to a fitting 301 using an adapter 501, according to an embodiment. The system 400 may provide for, via the patient's mouth, the delivery and/or extraction of oxygen or other medical gases (e.g., anesthetic gases) from a patient's airway, as well as measurement of levels or concentrations of another gas or gases, for example, carbon dioxide, in the patient's airway.

The system 400 may include the oral airway 401, the adapter 501, and the fitting 301. The oral airway 401 may have a profile and geometry to fit into a patient's oral cavity and/or airway. The oral airway, sometimes referred to as an oropharyngeal airway, may be an airway adjunct, which may be used to maintain or open a patient's airway by stopping the patient's tongue from covering the patient's epiglottis. The oral airway may be, for example, a single channel oral airway, or a multi-channel oral airway (e.g., a dual-channel oral airway). The profile of the oral airway 401 may be, for example, curved, to fit and be insertable into a patient's oral cavity and airway via the patient's mouth. The fitting 301 may have a nozzle 302 and a port 303. The nozzle 302 may be sized to receive a medical tubing, for example, for the delivery of oxygen or other medical gases into the system 400. The oral airway 401 may have a flange 404 to prevent over insertion or slippage, and the adapter 501 may fit into an end of the oral airway 401 proximate the flange 404. To effect this, the oral airway 401 may have a female receiver at an end which may receive a male connector of the adapter 501. The adapter 501 may have a socket which may receive a male connector of the fitting 301.

The oral airway 401 may have dual channels. A first channel 402 may provide for the delivery and/or extraction of gases to or from a desired point (e.g., an insertion depth) within a patient's airway. A second channel 403 may provide for measuring a concentration of a gas (e.g., carbon dioxide) at the desired point in the patient's airway. The second channel 403 may be in communication with, for example the port 303 of the fitting 301.

Figure 2A:
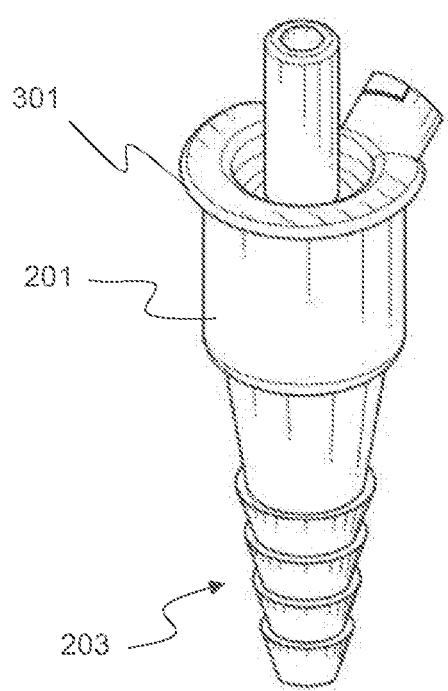
FIG. 2A illustrates a nasal trumpet adapter connected to a fitting, according to an embodiment.

FIG. 2A illustrates a nasal trumpet adapter 201 connected to a fitting 301, according to an embodiment. The adapter 201 may fit into a variety of nasal trumpets. The adapter 201 may be secured to a nasal trumpet by one or more integral barbs 203 disposed about a male end of the adapter 201. The adapter 201 may thus be used to connect a fitting 301 to a nasal trumpet.

Figure 2B:
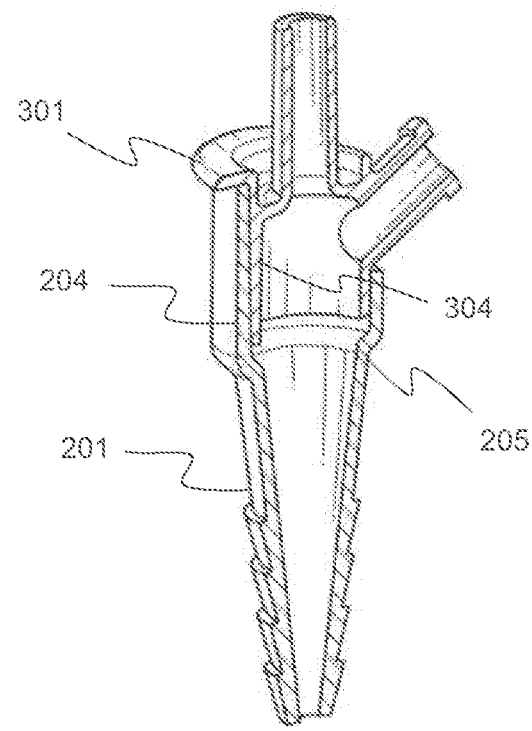
FIG. 2B illustrates a cross section view of a nasal trumpet adapter connected to a fitting, according to an embodiment.

FIG. 2B illustrates a cross section view of a nasal trumpet adapter 201 connected to a fitting 301, according to an embodiment. The adapter 201 may fit into a variety of nasal trumpets. The adapter 201 may connect to the fitting 301 via a male-female connection. The adapter 201 may have an upper wall 204, which may compose a socket sized to receive a male connection defined by a wall 304 of the fitting 301. The adapter 201 may further have an internal ridge 205, which may prevent over-insertion of the fitting 301.

Figure 2C:
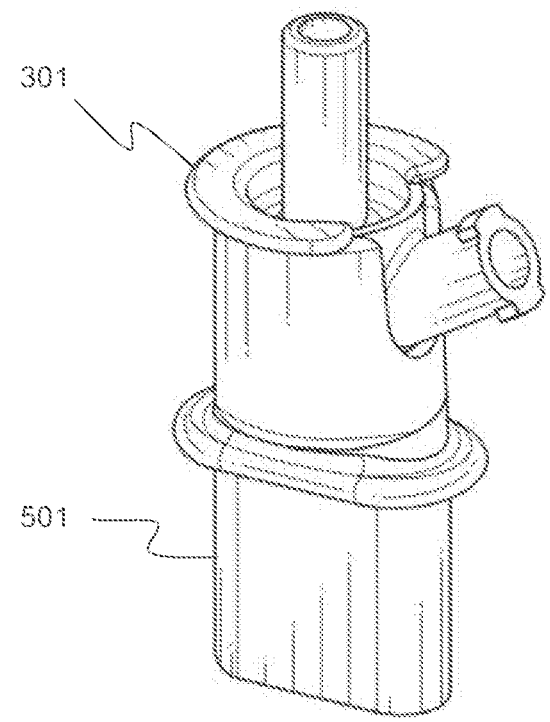
FIG. 2C illustrates an oral airway adapter connected to a fitting, according to an embodiment.

FIG. 2C illustrates an oral airway adapter 501 connected to a fitting 301, according to an embodiment. The adapter 501 may fit into a variety of oral airways. The adapter 501 may be secured to an oral airway by press-fitting a male end of the adapter 501 into a female receiver of an oral airway. The adapter 501 may thus be used to connect a fitting 301 to an oral airway.

Figure 2D:
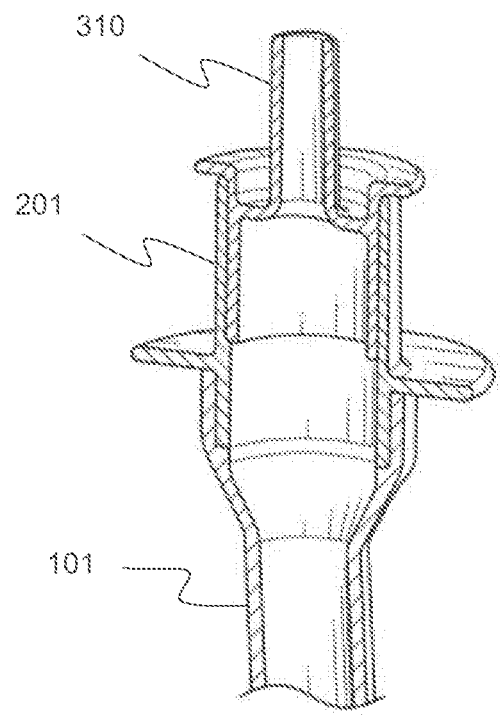
FIG. 2D illustrates a cross section view of a nasal trumpet adapter connected to a fitting, according to an embodiment.

FIG. 2D illustrates a cross section view of a nasal trumpet adapter 201 connected to a straight fitting 310, according to an embodiment. The straight fitting 310 may provide for the delivery and/or extraction of gases from the nasal trumpet 101 without an additional port. The adapter 201 may receive the straight nozzle fitting 310. In this way, the adapter 201 and the straight fitting 310 may provide for connecting a variety of medical circuits to the nasal trumpet 101.

Figure 2E:
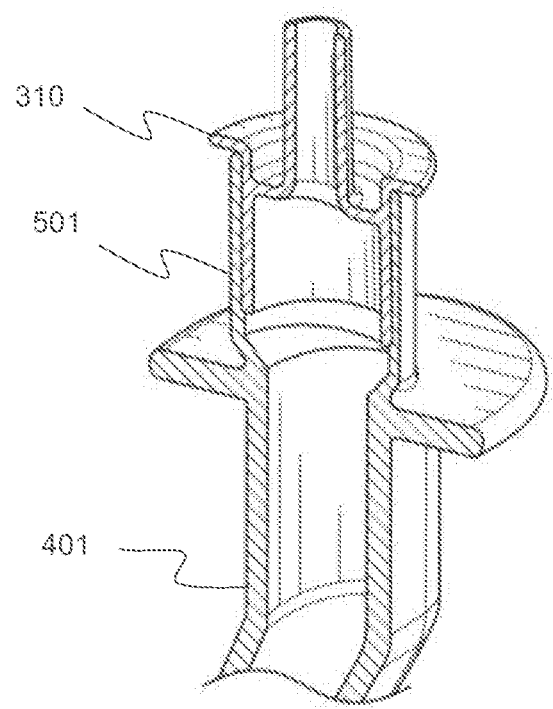
FIG. 2E illustrates a cross section view of an oral airway adapter connected to a fitting, according to an embodiment.

FIG. 2E illustrates a cross section view of an oral airway adapter 501 connected to a straight fitting 310, according to an embodiment. The straight fitting 310 may provide for the delivery and/or extraction of gases from the oral airway 401 without an additional port. The adapter 501 may receive the straight nozzle fitting 310. In this way, the adapter 501 and the straight fitting 310 may provide for connecting a variety of medical circuits to the oral airway 401. In some embodiments, the adapter 501 may be integral to the oral airway 401.

Figure 2F:
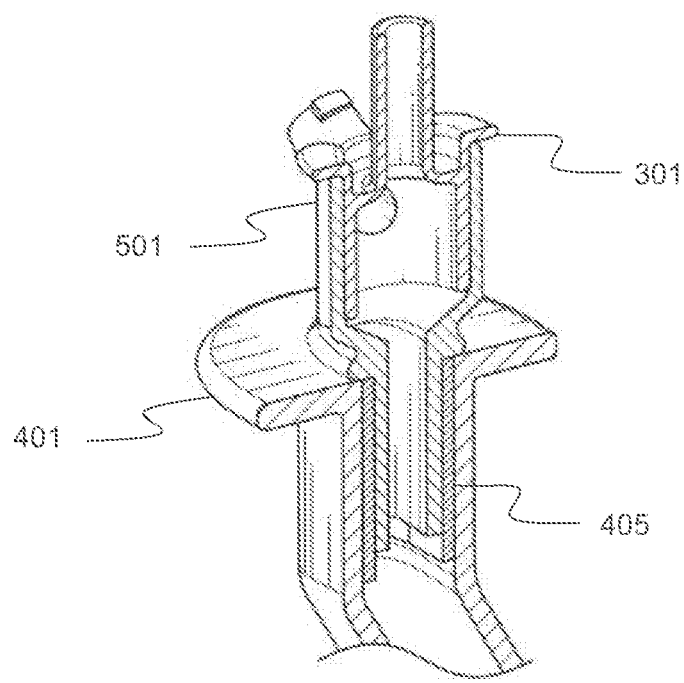
FIG. 2F illustrates a cross section view of an oral airway adapter connected to a fitting, according to an embodiment.

FIG. 2F illustrates a cross section view of an oral airway adapter 501 connected to a fitting 301, according to an embodiment. The adapter 501 may be used to connect a variety of medical fittings to a stock oral airway. The connector 501 may receive a fitting 301 and further fit into a standard female receptacle, for example a receptacle 405 of an oral airway 401.

Figure 2G:
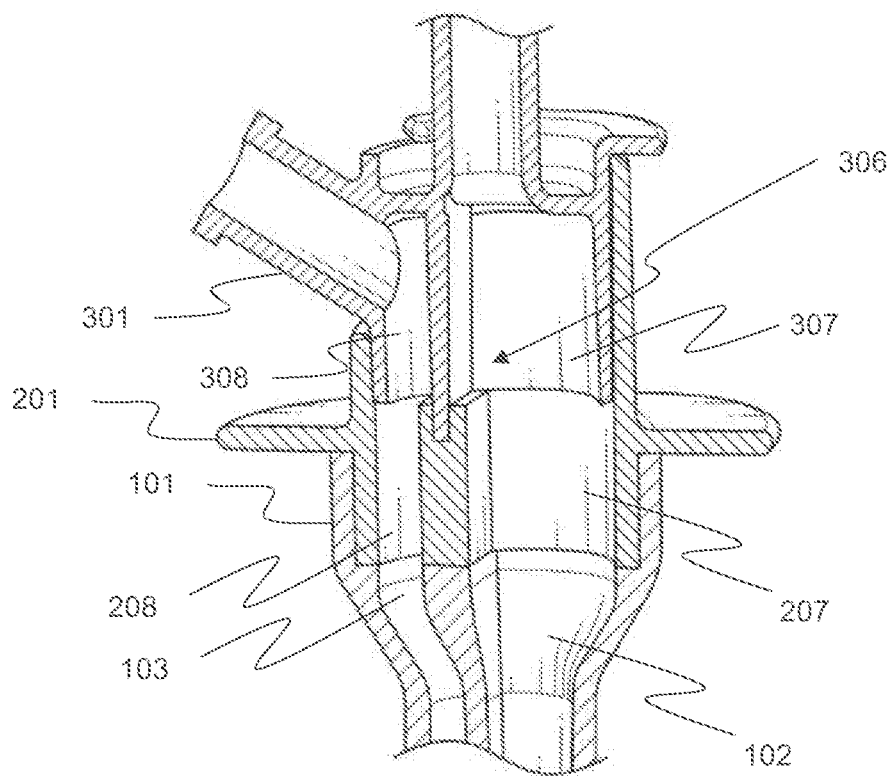
FIG. 2G illustrates a cross section view of a nasal trumpet adapter connected to a fitting, according to an embodiment.

FIG. 2G illustrates a cross section view of a nasal trumpet adapter 201 connected to a fitting 301, according to an embodiment. The dual channel configuration illustrated in FIG. 2G may provide for concurrent delivery and/or extraction of gases from a desired point in a patient's airway as well as measurement of a gas concentration, for example, carbon dioxide, at the desired point in the patient's airway.

The nasal trumpet 101 may have a first channel 102 and a second channel 103 which may be separated by a partition wall. The adapter 201 may have a first channel 207, which may share a cross section with a portion of the first channel 102 of the nasal trumpet 101. The adapter 201 may have a second channel 208, the cavity defined by which may have a similar cross section with a cavity defined by a portion of the second channel 103 of the nasal trumpet 101.

The fitting 301 may have a first channel 307, the cavity defined by which may have a similar cross section with a cavity defined by a portion of the first channel 207 of the adapter 201. The fitting 301 may have a second channel 308, the cavity defined by which may have a similar cross section with a cavity defined by a portion of the second channel 308 of the adapter 201.

The fitting 301 may form a seal with the adapter 201 at a joint 306. For example, the joint 306 may be a tongue-and-groove joint. In this example, the adapter 201 may have a partition wall with a groove at an end exposed to the fitting 301 and a partition wall of the fitting 301 may have a tongue extending therefrom, which may fit into the groove of the partition wall of the adapter 201. In this way, a substantially airtight seal may be formed to separate gases within the first channels 102, 207, and 307 from those gases in the second channels 103, 208, and 308.

Figure 3A:
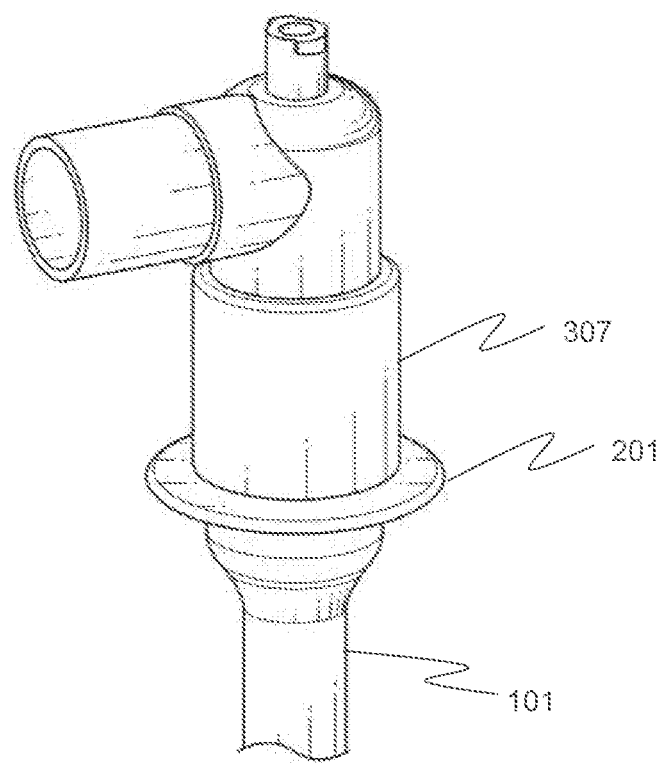
FIG. 3A illustrates a cross section view of a nasal trumpet adapter connected to an elbow fitting, according to an embodiment.

FIG. 3A illustrates a cross section view of a nasal trumpet adapter 201 connected to an elbow fitting 307, according to an embodiment. The adapter 201 may provide for the connection of various fittings, such as, for example, the elbow fitting 307.

The elbow fitting 307 may fit onto one end of the adapter 201 and the adapter 201 may fit as described herein with a nasal trumpet 101. The elbow fitting 307 may be a fitting of various angles, for example, the elbow fitting 307 may be, inter alia, a 90 degree fitting, a 60 degree fitting, a 45 degree fitting, or an irregular-contour fitting. The elbow fitting 307 may provide for routing of connected tubing in a predefined direction other than straight out of the nasal trumpet 101. In this way, the adapter 201 and the elbow fitting 307 may provide for the delivery and/or extraction of oxygen or other medical gases from a desired point within the patient's airway via a variety of external medical connections.

Figure 3B:
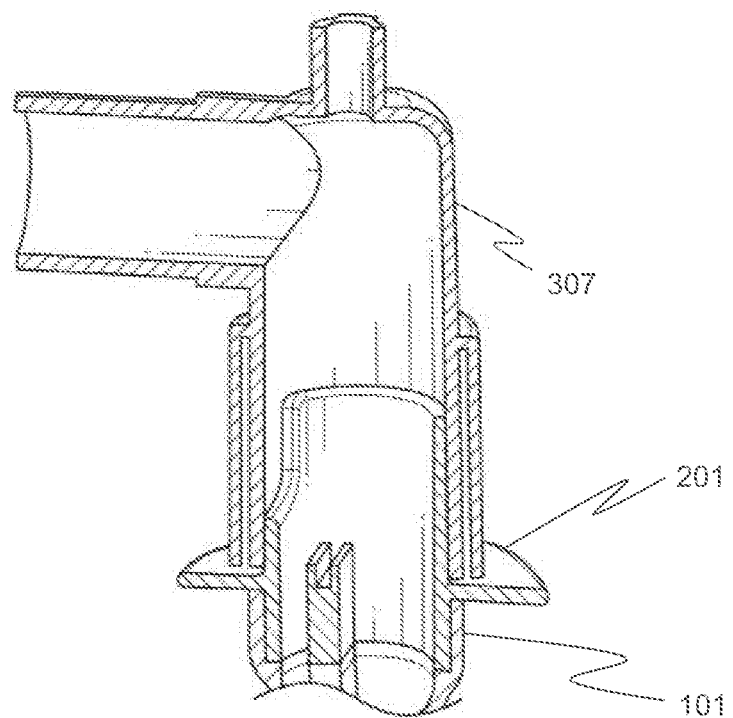
FIG. 3B illustrates a cross section view of a nasal trumpet adapter connected to an elbow fitting, according to an embodiment.

FIG. 3B illustrates a cross section view of a nasal trumpet adapter 201 connected to an elbow fitting 307, according to an embodiment. A fitting need not require the use of dual channels, even though the nasal trumpet 101 and the adapter 201 provide for the capability of doing so.

A fitting, for example, the elbow fitting 307, may be installed onto the adapter 201, which may itself have a plurality of channels (e.g., dual channels). Since the elbow fitting 307 does not utilize dual channels, both channels (e.g., channels 102, 103, 207, and 208) of the adapter 201 and the nasal trumpet 101 may be utilized to develop a total flow of a gas via the elbow 307.

Figure 4:
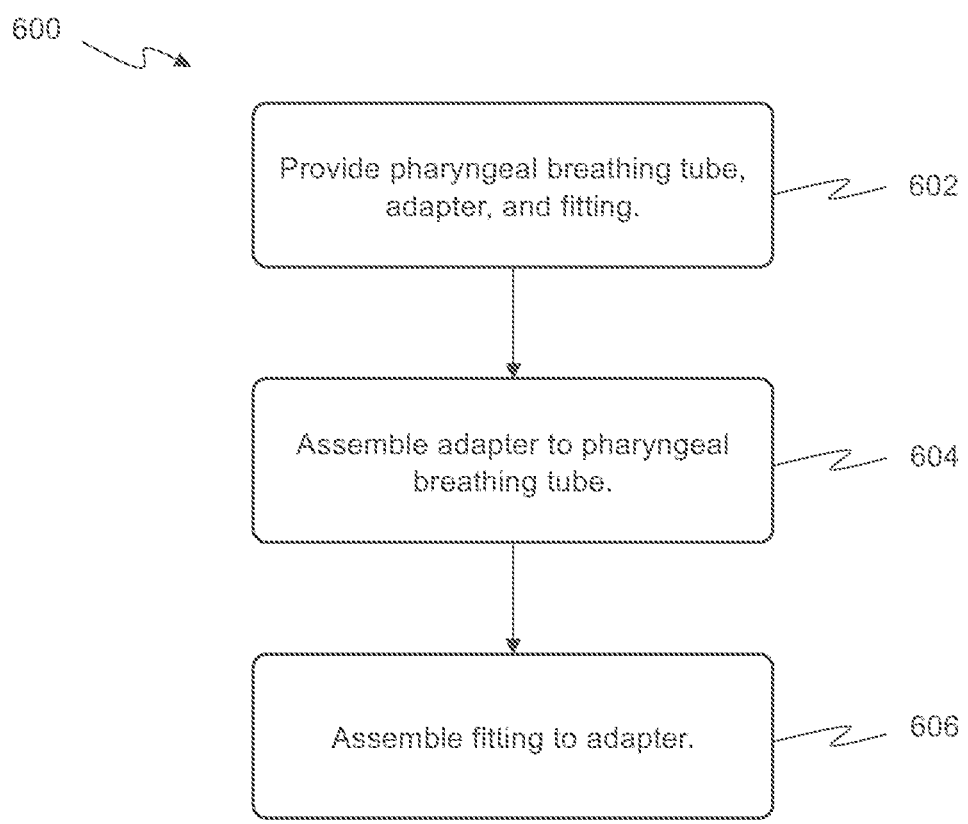
FIG. 4 illustrates a method of assembling an adapter and a fitting to a pharyngeal breathing tube, according to an embodiment.

FIG. 4 illustrates a method 600 of assembling an adapter and a fitting to a pharyngeal breathing tube, according to an embodiment. The method 600 may thus provide for the assembly of a system, for example the system 100 or the system 400, which may be used with the delivery and/or extraction of gases from a desired point in a patient's airway.

At 602, a pharyngeal breathing tube, and adapter, and a fitting may be provided. The pharyngeal breathing tube may be, for example, a nasal trumpet (e.g., the nasal trumpet 101) or an oral airway (e.g., the oral airway 401). The adapter may be an adapter as described herein (e.g., the adapter 301). The fitting may be one or more of a variety of fittings (e.g., the fitting 301 or the elbow fitting 307), which may be used to connect the system to an exterior medical circuit. At 604, the adapter may be assembled to the pharyngeal breathing tube. At 606, the fitting may be assembled to the adapter.

Various components, including, but not limited to, one or more of the adapter, the fitting, and the pharyngeal breathing tube (e.g., the nasal trumpet or oral airway), or various portions thereof, may be constructed of a plastic (e.g., ABS, polylactic acid (PLA), polycarbonate (PG), polyethylene terephthalate (PET, PETT, PETG, PETE), nylon, high density polyethylene (HDPE), polyvinyl chloride (PVC), low density polyethylene (LDPE), polypropylene (PP), or polystyrene, or other suitable plastics), a silicone (e.g., siloxane), a metal (e.g., stainless steel, surgical steel), a composite material (e.g., carbon fiber), or another suitable material.

In an aspect, a system may include a pharyngeal breathing tube, a medical fitting, and an adapter. The pharyngeal breathing tube may include an insertion end; a body; a receiving end; a receiver proximate the receiving end for receiving an adapter. The insertion end may be inserted into the patient's airway via the patient's nose or mouth such that the receiving end remains external to the patient's airway.

The body may be curved such that it fits into the patient's airway. The medical fitting may include a nozzle configured to receiving a medical circuit tube in fluid communication with a medical gas supply and a port configured to receiving an accessory tube or a gas measurement device. The adapter may include a connection end having a first outer width, wherein the connection end may be disposed within the receiver of the pharyngeal breathing tube, a flange disposed on the connection end having a second outer width greater than the first outer width, wherein the flange does not fit within the receiving end of the pharyngeal breathing tube, and a socket disposed on the flange. The socket may include a notch receiving the port of the medical fitting. The medical fitting may be received by the socket. A partition wall may be disposed within the connection end. The connection end, the flange, and the socket may form a tubular structure having a first end including the connection end and a second end including the socket. The partition wall may separate a first channel for communicating a medical gas and a second channel for measuring a concentration of carbon dioxide within the tubular structure. The partition wall may align with a divider of the pharyngeal breathing tube.

The medical fitting may include a fitting divider aligned with the partition wall of the adapter.

The partition wall of the adapter may include a groove. The fitting divider of the medical fitting may include a tongue extending therefrom for insertion into the groove. The groove of the partition wall of the adapter may receive the tongue of the fitting divider of the medical fitting.

The connection end may include one or more barbs. The barbs may be disposed about an exterior surface of the connection end. The barbs may be disposed within the receiver of the pharyngeal breathing tube.

The pharyngeal breathing tube may include a nasal trumpet or an oral airway. The pharyngeal breathing tube may have a first channel for communicating a medical gas and a second channel for measuring a concentration of carbon dioxide within the pharyngeal breathing tube.

In another aspect, a method may include providing a pharyngeal breathing tube, a medical fitting, and an adapter. The method may further include assembling the adapter to the pharyngeal breathing tube, including inserting the connection end of the adapter into the receiver of the pharyngeal breathing tube to an insertion depth such that the flange may be disposed on the receiving end of the pharyngeal tube. The method may further include assembling the medical fitting to the adapter, including inserting the medical fitting into the socket of the adapter. The pharyngeal breathing tube may include an insertion end; a body; a receiving end; a receiver proximate the receiving end for receiving an adapter. The insertion end may be inserted into the patient's airway via the patient's nose or mouth such that the receiving end remains external to the patient's airway. The body may be curved such that it fits into the patient's airway. The medical fitting may include a nozzle configured to receiving a medical circuit tube in fluid communication with a medical gas supply and a port configured to receiving an accessory tube or a gas measurement device. The adapter may include a connection end having a first outer width, wherein the connection end may be disposed within the receiver of the pharyngeal breathing tube, a flange disposed on the connection end having a second outer width greater than the first outer width, wherein the flange does not fit within the receiving end of the pharyngeal breathing tube, and a socket disposed on the flange.

Assembling the adapter to the pharyngeal breathing tube may further include rotating the adapter such that the partition wall and the divider are aligned.

The medical fitting may further include a port and a fitting divider. The fitting divider may separate a third channel and a fourth channel, the third channel corresponding to the first channel and the fourth channel corresponding to the second channel. The port may be in fluid communication with the fourth channel. The method may further include assembling a gas measurement device to the port, wherein the gas measurement device may measure a level of carbon dioxide, oxygen, or anesthetic gas in the fourth channel.

The method may further include inserting at least a portion of the pharyngeal breathing tube into a nose of a patient, wherein the pharyngeal breathing tube may include a nasal trumpet. The method may further include inserting at least a portion of the pharyngeal breathing tube into a mouth of a patient, wherein the pharyngeal breathing tube may include an oral airway.

An apparatus may include a connection end having a first outer width, wherein the connection end may be insertably disposed within a receiver of a pharyngeal breathing tube; a flange disposed on the connection end having a second outer width greater than the first outer width, wherein the flange may not fit within the receiver of the pharyngeal breathing tube; and a socket disposed on the flange, wherein the socket may receive a medical fitting.

The connection end may include one or more barbs disposed about an exterior surface of the connection end and may be insertably disposed within the receiver of the pharyngeal breathing tube such that an insertion force required for inserting the connection end into the receiver of the pharyngeal breathing tube may be less than an extraction force required for extracting the connection end from the receiver of the pharyngeal breathing tube. Each barb of the one or more barbs may be disposed within a corresponding depression about an internal surface of the receiver of the pharyngeal breathing tube. The extraction force may exceed a tensile strength of the connection end, the flange, or the socket.

The connection end may be configured with a circular cross-section. The pharyngeal breathing tube may include a nasal trumpet. The receiver of the nasal trumpet may be configured with a circular cross-section.

The connection end may be configured with an oval cross-section. The pharyngeal breathing tube may include an oral airway. The receiver of the oral airway may be configured with an oval cross-section.

The socket may further include an internal ridge, which may limit an insertion depth of the medical fitting into the socket.

A feature illustrated in one of the figures may be the same as or similar to a feature illustrated in another of the figures. Similarly, a feature described in connection with one of the figures may be the same as or similar to a feature described in connection with another of the figures. The same or similar features may be noted by the same or similar reference characters unless expressly described otherwise. Additionally, the description of a particular figure may refer to a feature not shown in the particular figure. The feature may be illustrated in and/or further described in connection with another figure.

Elements of processes (i.e., methods) described herein may be executed in one or more ways such as by a human, by a processing device, by mechanisms operating automatically or under human control, and so forth. Additionally, although various elements of a process may be depicted in the figures in a particular order, the elements of the process may be performed in one or more different orders without departing from the substance and spirit of the disclosure herein.

The foregoing description sets forth numerous specific details such as examples of specific systems, components, methods and so forth, in order to provide a good understanding of several implementations. It will be apparent to one skilled in the art, however, that at least some implementations may be practiced without these specific details. In other instances, well-known components or methods are not described in detail or are presented in simple block diagram format in order to avoid unnecessarily obscuring the present implementations. Thus, the specific details set forth above are merely exemplary. Particular implementations may vary from these exemplary details and still be contemplated to be within the scope of the present implementations.

Related elements in the examples and/or embodiments described herein may be identical, similar, or dissimilar in different examples. For the sake of brevity and clarity, related elements may not be redundantly explained. Instead, the use of a same, similar, and/or related element names and/or reference characters may cue the reader that an element with a given name and/or associated reference character may be similar to another related element with the same, similar, and/or related element name and/or reference character in an example explained elsewhere herein. Elements specific to a given example may be described regarding that particular example. A person having ordinary skill in the art will understand that a given element need not be the same and/or similar to the specific portrayal of a related element in any given figure or example in order to share features of the related element.

It is to be understood that the foregoing description is intended to be illustrative and not restrictive. Many other implementations will be apparent to those of skill in the art upon reading and understanding the above description. The scope of the present implementations should, therefore, be determined with reference to the appended claims, along with the full scope of equivalents to which such claims are entitled.

The foregoing disclosure encompasses multiple distinct examples with independent utility. While these examples have been disclosed in a particular form, the specific examples disclosed and illustrated above are not to be considered in a limiting sense as numerous variations are possible. The subject matter disclosed herein includes novel and non-obvious combinations and sub-combinations of the various elements, features, functions and/or properties disclosed above both explicitly and inherently. Where the disclosure or subsequently filed claims recite "a" element, "a first" element, or any such equivalent term, the disclosure or claims is to be understood to incorporate one or more such elements, neither requiring nor excluding two or more of such elements.

As used herein "same" means sharing all features and "similar" means sharing a substantial number of features or sharing materially important features even if a substantial number of features are not shared. As used herein "may" should be interpreted in a permissive sense and should not be interpreted in an indefinite sense. Additionally, use of "is" regarding examples, elements, and/or features should be interpreted to be definite only regarding a specific example and should not be interpreted as definite regarding every example. Furthermore, references to "the disclosure" and/or "this disclosure" refer to the entirety of the writings of this document and the entirety of the accompanying illustrations, which extends to all the writings of each subsection of this document, including the Title, Background, Brief description of the Drawings, Detailed Description, Claims, Abstract, and any other document and/or resource incorporated herein by reference.

As used herein regarding a list, "and" forms a group inclusive of all the listed elements. For example, an example described as including A, B, C, and D is an example that includes A, includes B, includes C, and also includes D. As used herein regarding a list, "or" forms a list of elements, any of which may be included. For example, an example described as including A, B, C, or D is an example that includes any of the elements A, B, C, and D. Unless otherwise stated, an example including a list of alternatively-inclusive elements does not preclude other examples that include various combinations of some or all of the alternatively-inclusive elements. An example described using a list of alternatively-inclusive elements includes at least one element of the listed elements. However, an example described using a list of alternatively-inclusive elements does not preclude another example that includes all of the listed elements. And, an example described using a list of alternatively-inclusive elements does not preclude another example that includes a combination of some of the listed elements. As used herein regarding a list, "and/or" forms a list of elements inclusive alone or in any combination. For example, an example described as including A, B, C, and/or D is an example that may include: A alone; A and B; A, B and C; A, B, C, and D; and so forth. The bounds of an "and/or" list are defined by the complete set of combinations and permutations for the list.

Where multiples of a particular element are shown in a FIG., and where it is clear that the element is duplicated throughout the FIG., only one label may be provided for the element, despite multiple instances of the element being present in the FIG. Accordingly, other instances in the FIG. of the element having identical or similar structure and/or function may not have been redundantly labeled. A person having ordinary skill in the art will recognize based on the disclosure herein redundant and/or duplicated elements of the same FIG. Despite this, redundant labeling may be included where helpful in clarifying the structure of the depicted examples.

The Applicant(s) reserves the right to submit claims directed to combinations and sub-combinations of the disclosed examples that are believed to be novel and non-obvious. Examples embodied in other combinations and sub-combinations of features, functions, elements and/or properties may be claimed through amendment of those claims or presentation of new claims in the present application or in a related application. Such amended or new claims, whether they are directed to the same example or a different example and whether they are different, broader, narrower or equal in scope to the original claims, are to be considered within the subject matter of the examples described herein.

The invention claimed is:

1. A system, comprising:
   a pharyngeal breathing tube, comprising:
      an insertion end;
      a body;
      a receiving end;
      a receiver proximate the receiving end for receiving an adapter;
      wherein the insertion end is configured to be inserted into an airway of a patient via a nose or a mouth of the patient such that the receiving end remains external to the airway; and
wherein the body is curved such that it is configured to fit into the airway;
a medical fitting, comprising:
a nozzle configured to receiving a medical circuit tube in fluid communication with a medical gas supply; and
a port configured to receive an accessory tube or a gas measurement device; and
the adapter, comprising:
a connection end having a first outer width, wherein the connection end is disposed within the receiver of the pharyngeal breathing tube;
a flange disposed on the connection end having a second outer width greater than the first outer width, wherein the flange does not fit within the receiving end of the pharyngeal breathing tube; and
a socket disposed on the flange, comprising:
a notch configured to receive the port of the medical fitting; and
wherein the medical fitting is received by the socket; and
a partition wall disposed within the connection end; and wherein:
the connection end, the flange, and the socket form a tubular structure having a first end comprising the connection end and a second end comprising the socket;
the partition wall separates a first channel for communicating a medical gas and a second channel for measuring a concentration of carbon dioxide within the tubular structure; and
the partition wall is configured to align with a divider of the pharyngeal breathing tube.

2. The system of claim 1, wherein the medical fitting comprises a fitting divider aligned with the partition wall of the adapter.

3. The system of claim 2, wherein:
the partition wall of the adapter comprises a groove; and
the fitting divider of the medical fitting comprises a tongue extending therefrom for insertion into the groove; and
wherein the groove of the partition wall of the adapter receives the tongue of the fitting divider of the medical fitting.

4. The system of claim 1, wherein the connection end includes one or more barbs:
disposed about an exterior surface of the connection end; and
disposed within the receiver of the pharyngeal breathing tube.

5. The system of claim 1, wherein:
the pharyngeal breathing tube comprises a nasal trumpet or an oral airway; and
the pharyngeal breathing tube comprises:
the first channel for communicating the medical gas; and
the second channel for measuring the concentration of carbon dioxide within the pharyngeal breathing tube.

6. A method, comprising:
providing a pharyngeal breathing tube, comprising:
an insertion end;
a body;
a receiving end;
a receiver proximate the receiving end for receiving an adapter;
wherein the insertion end is configured to be inserted into an airway of the patient via a nose or a mouth of the patient such that the receiving end remains external to the airway; and
wherein the body is curved such that it is configured to fit into the airway;
providing a medical fitting;
providing the adapter, comprising:
a connection end having a first outer width, wherein the connection end is configured to be insertably disposed within the receiver of the pharyngeal breathing tube;
a flange disposed on the connection end having a second outer width greater than the first outer width, wherein the flange is configured to not fit within the receiving end of the pharyngeal breathing tube; and
a socket disposed on the flange, the socket comprising a notch configured to receive a port of the medical fitting; and wherein the socket is configured to receive the medical fitting;
wherein the connection end, the flange, and the socket form a tubular structure having a first end comprising the connection end and a second end comprising the socket;
wherein the pharyngeal breathing tube further comprises a partition wall disposed within the connection end;
wherein the partition wall separates a first channel for communicating a medical gas and a second channel for measuring a concentration of carbon dioxide within the pharyngeal breathing tube; and
wherein the partition wall is configured to align with a divider of the pharyngeal breathing tube;
assembling the adapter to the pharyngeal breathing tube, comprising:
inserting the connection end of the adapter into the receiver of the pharyngeal breathing tube to an insertion depth such that the flange is disposed on the receiving end of the pharyngeal tube; and
assembling the medical fitting to the adapter, comprising:
inserting the medical fitting into the socket of the adapter.

7. The method of claim 6, wherein
assembling the adapter to the pharyngeal breathing tube further comprises rotating the adapter such that the partition wall and the divider are aligned.

8. The method of claim 6, wherein:
the medical fitting further comprises a nozzle;
the method further comprises assembling a medical circuit tube to the nozzle; and
the medical circuit tube is in fluid communication with a medical gas supply.

9. The method of claim 8, wherein: the medical fitting further comprises a fitting divider;
the fitting divider separates a third channel and a fourth channel, the third channel corresponding to the first channel and the fourth channel corresponding to the second channel;
the port is in fluid communication with the fourth channel; and
the method further comprises assembling a gas measurement device to the port, wherein the gas measurement device is configured to measure a level of carbon dioxide, oxygen, or anesthetic gas in the fourth channel.

10. The method of claim 6, further comprising:
inserting at least a portion of the pharyngeal breathing tube into a nose of a patient, wherein the pharyngeal breathing tube comprises a nasal trumpet; or
inserting at least a portion of the pharyngeal breathing tube into the mouth of the patient, wherein the pharyngeal breathing tube comprises an oral airway.

11. An apparatus, comprising:
a connection end having a first outer width, wherein the connection end is configured to be insertably disposed within a receiver of a pharyngeal breathing tube;
a flange disposed on the connection end having a second outer width greater than the first outer width, wherein the flange is configured to not fit within the receiver of the pharyngeal breathing tube; and
a socket disposed on the flange comprising a notch configured to receive a port of the medical fitting, wherein:
the socket is configured to receive the medical fitting;
a partition wall disposed within the connection end, wherein:
the partition wall separates a first channel for communicating a medical gas and a second channel for measuring a concentration of carbon dioxide within the pharyngeal breathing tube; and
the partition wall is configured to align with a divider of the pharyngeal breathing tube;
wherein the medical fitting comprises a nozzle configured to receiving a medical circuit tube in fluid communication with a medical gas supply; and
wherein the connection end, the flange, and the socket form a tubular structure having a first end comprising the connection end and a second end comprising the socket.

12. The apparatus of claim 11 wherein the partition wall comprises a groove configured to receive a tongue of a fitting divider of the medical fitting.

13. The apparatus of claim 11, wherein the connection end includes one or more barbs disposed about an exterior surface of the connection end and configured to be insertably disposed within the receiver of the pharyngeal breathing tube such that an insertion force required for inserting the connection end into the receiver of the pharyngeal breathing tube is less than an extraction force required for extracting the connection end from the receiver of the pharyngeal breathing tube.

14. The apparatus of claim 13, wherein at least one barb of the one or more barbs is configured to be disposed within a corresponding depression about an internal surface of the receiver of the pharyngeal breathing tube.

15. The apparatus of claim 13, wherein the extraction force exceeds a tensile strength of the connection end, the flange, or the socket.

16. The apparatus of claim 11, wherein:
the connection end is configured with a circular cross-section;
the pharyngeal breathing tube comprises a nasal trumpet; and
the receiver of the nasal trumpet is configured with a circular cross-section.

17. The apparatus of claim 11, wherein:
the connection end is configured with an oval cross-section;
the pharyngeal breathing tube comprises an oral airway; and
the receiver of the oral airway is configured with an oval cross-section.

18. The apparatus of claim 11, wherein the socket further comprises an internal ridge configured to limit an insertion depth of the medical fitting into the socket.

* * * * *